(12) United States Patent
Castor

(10) Patent No.: US 7,147,806 B2
(45) Date of Patent: Dec. 12, 2006

(54) POLYMER MICROSPHERES/NANOSPHERES AND ENCAPSULATING THERAPEUTIC PROTEINS THEREIN

(75) Inventor: Trevor P. Castor, Arlington, MA (US)

(73) Assignee: Aphios Corporation, Woburn, MA (US)

(*) Notice: Subject to any disclaimer, the term of this patent is extended or adjusted under 35 U.S.C. 154(b) by 0 days.

(21) Appl. No.: 10/840,308

(22) Filed: May 6, 2004

(65) Prior Publication Data

US 2006/0033224 A1    Feb. 16, 2006

Related U.S. Application Data

(63) Continuation of application No. 09/750,473, filed on Dec. 29, 2000, now abandoned.

(51) Int. Cl.
*B29B 9/10* (2006.01)

(52) U.S. Cl. .............. 264/13; 264/5; 264/12; 425/6

(58) Field of Classification Search .......... 264/5, 264/12, 13; 425/6
See application file for complete search history.

(56) References Cited

U.S. PATENT DOCUMENTS 4,582,731 A * 4/1986 Smith .................. 427/427
4,734,451 A * 3/1988 Smith .................. 524/493
5,043,280 A * 8/1991 Fischer et al. .......... 435/235.1
5,554,382 A * 9/1996 Castor ................. 424/450
5,766,637 A * 6/1998 Shine et al. ............. 424/497
6,124,226 A * 9/2000 Nielsen et al. ............ 502/9

OTHER PUBLICATIONS

Langer, R., Cima, L.G., Tamada, J.A. and Wintermantel, E. "Future Directions in Biomaterials", *Biomaterials*, 11:738-745 (1990).
Mathiowitz, E., Jacob, J.S., Jong, Y.S., Carino, G.P., Chickering, D.E., Chaturvadi, P., Santos, C.A., Vijaaraghavan, K., Montgomery, S., Bassett, M. and Morrell, C. "Biologically Erodable Microspheres as Potential Oral Drug Delivery Systems", *Nature*, 386:410-414 (1997).

* cited by examiner

*Primary Examiner*—Mary Lynn Theisen
(74) *Attorney, Agent, or Firm*—Burns & Levinson, LLP; Stephen J. Gaudet; Janine M. Susan

(57) ABSTRACT

This invention is for an improved process to formulate polymeric microspheres/nanospheres and encapsulate therapeutic proteins and other useful substances. Non-toxic supercritical or near-critical fluids with/without polar cosolvents are utilized to solubilize biodegradable polymers and form uniform polymer microspheres and nanospheres to encapsulate proteins with controlled-release characteristics.

17 Claims, 3 Drawing Sheets

US 7,147,806 B2

POLYMER MICROSPHERES/NANOSPHERES AND ENCAPSULATING THERAPEUTIC PROTEINS THEREIN

RELATED APPLICATIONS

This application is a continuation of, claims priority to and the benefit of U.S. application Ser. No. 09/750,473, filed Dec. 29, 2000, now abandoned.

FIELD OF THE INVENTION

This invention relates to methods for making polymer microspheres and nanospheres and encapsulating therapeutic proteins and other products. The methods relate to improving the drug delivery of therapeutics and other products, and to making therapeutic proteins and other products more orally bioavailable. The methods feature supercritical, critical and near critical fluids with and without polar cosolvents.

BACKGROUND OF THE INVENTION

Conventional methods of drug delivery such as tablets or injections provide an initial spike of therapeutic agent in a subject's system followed by a period of decay. Dosage is frequently limited by adverse side effects engendered by the elevated, albeit temporary, high level of agent. Furthermore, as the agent is cleared from the body, its concentration will most likely fall below a useful level prior to the next treatment. For many drugs, the ideal is a steady level over a prolonged period ranging from hours to years. This type of profile can be attained with the use of controlled release technology. Improved techniques for controlled release of therapeutic agents is an area of great importance to the medical field, the pharmaceutical industry, and the public that they serve.

One of the most promising methods for controlled release involves the use of degradable or erodable polymers. Following administration via ingestion or injection, the polymer is slowly eroded by body fluids to yield biocompatible breakdown products. Concurrently, drug is released from a polymeric particle by diffusion through the polymer matrix as well as by surface erosion.

Supercritical fluids offer considerable promise as vehicles for the formation of polymeric particles of biomedical interest. Two techniques have been reported to date to formulate poly(L-lactic acid) (PLA) microparticles. In the first method, PLA is dissolved in the supercritical fluid, and particles are formed as a result of rapid expansion of the supercritical fluid. This process is known as rapid expansion of supercritical solution (RESS). RESS is a clear alternative to the conventional methods for the production of drug-loaded polymeric microparticles since it requires no surfactants, yields a solvent-free product, and allows rapid processing at moderate conditions. Therapeutics must be soluble in the supercritical fluid system used; however, most therapeutic proteins are not directly soluble in supercritical fluid systems.

In a second method, PLA is solubilized in the organic solvent and sprayed into the supercritical fluid continuous phase. Here supercritical fluid is used as an anti-solvent that causes particle precipitation from the liquid. This method is known as gas anti-solvent precipitation (GAS). The advantage of GAS over RESS is that the therapeutic agent does not have to be soluble in the supercritical fluid, but only in a suitable organic solvent. The solubility of most proteins in organic solvents is negligible, necessitating the use of large volumes of organic solvents. The disadvantage is that organic solvent must be utilized, although the amount of organic solvent used may be considerably less than with conventional processes.

In addition to reduction or elimination of organic solvent usage, use of supercritical fluids for the production of polymer microspheres and nanospheres can impart advantages of product sterility.

At present, large-scale production of polymeric microspheres utilize many processing steps and require large quantities of organic solvents. The process is very time consuming, costly and inefficient. Generally, such polymeric microspheres have a wide dispersion of particle size. Such polymeric spheres tend to have a median size greater than 100 microns in diameter. In addition, the exposure of therapeutic agent to the organic solvent may adversely affect the integrity of the final product. The organic solvent must be removed and the product may become contaminated with residual organic solvent that may be toxic. The process steps may also compromise sterility, or do not provide sterility.

SUMMARY OF THE INVENTION

The present invention is related to polymeric spheres and methods of using supercritical fluids for making uniform polymer spheres. The uniformity and integrity of such spheres make such spheres ideal for containing therapeutic agents such as biological molecules. The methods require reduced processing time and preparation costs.

In one embodiment of the present invention, a method of making polymeric spheres comprising the steps of providing a polymer solution of a polymeric material dissolved in a first fluid is disclosed. In one aspect, the first fluid comprises a supercritical, critical or near-critical fluid. Next, the polymer solution is depressurized as the polymer solution exits one or more orifices of an apparatus in the presence of a low solubility fluid. The low solubility fluid has low volatility and the polymeric material is in a concentration which exceeds the solubility of the polymeric material in the low solubility fluid. The polymeric material forms spheres and the first fluid is removed during depressurization.

In another embodiment, a method for incorporating bioactive materials in polymeric spheres is disclosed. A polymeric material is contacted with a first fluid. This first fluid comprises a critical, supercritical, or near critical fluid with or without one or more cosolvents. This first admixture of polymeric material and first fluid are admixed with a second fluid forming a second admixture, wherein the second fluid comprises a bioactive or therapeutic agent. This second fluid can comprise a critical, supercritical, or near critical fluid together with a cosolvent such as an alcohol, an aqueous solvent such as distilled water or mixtures thereof. The second admixture is subjected to depressurization. This depressurization can be accomplished by releasing the second admixture through an orifice of the apparatus into a medium at, for example, atmospheric pressure. In one aspect, the medium into which the second admixture is released is a third fluid. This third fluid is a low solubility solvent.

A further embodiment of the present invention features an apparatus for forming one or more polymeric spheres. The apparatus comprises an admixture vessel, a depressurization chamber and an orifice. The admixture vessel is for receiving and containing a polymer solution of a polymeric material in a first fluid, the first fluid consisting of a supercritical, critical or near-critical fluid. The depressurization chamber contains a low solubility fluid and is in fluid communication with the admixture vessel by the orifice. The depressurization chamber receives the polymer solution as said polymer solution exits the orifices in the presence of a low solubility fluid. The low solubility fluid has low volatility and the polymeric material is in a concentration which exceeds its solubility in such fluid. The polymeric material forms spheres and the first fluid is removed during depressurization.

DETAILED DESCRIPTION OF THE INVENTION

Figure 1:
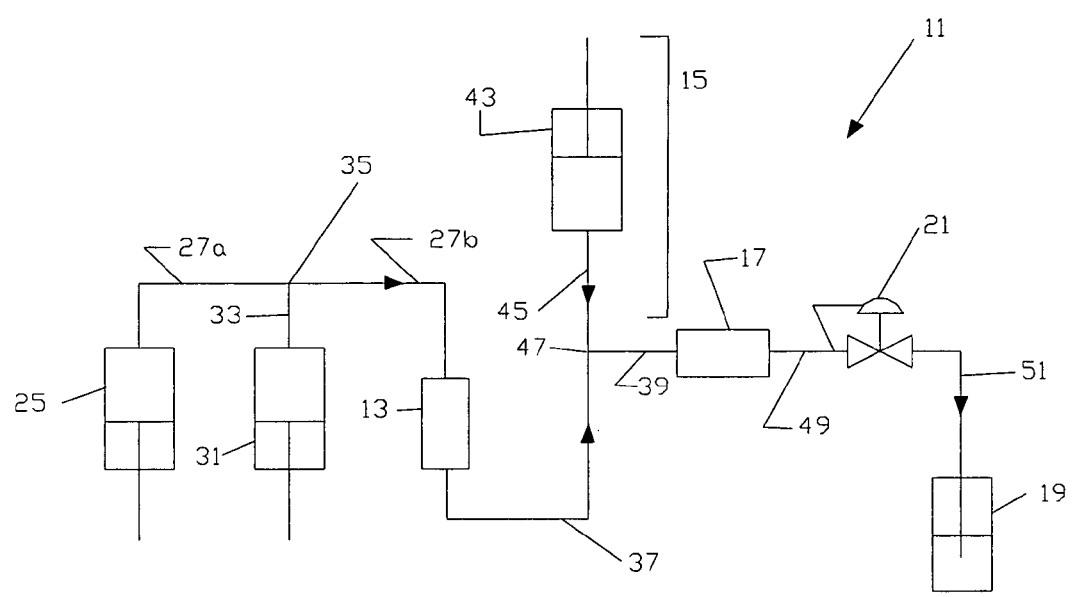
FIG. 1 depicts in schematic form an apparatus embodying features of the present invention.

The present invention is related to polymeric spheres and methods of using supercritical fluids for making uniform polymer spheres. The uniformity and integrity of such spheres make such spheres ideal for containing therapeutic agents such as biological molecules and pharmaceuticals. The methods require reduced processing time and preparation costs.

Aspects of the present invention employ materials known as supercritical, critical or near-critical fluids. A material becomes a critical fluid at conditions which equal its critical temperature and critical pressure. A material becomes a supercritical fluid at conditions which equal or exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero debyes.

A supercritical fluid displays a wide spectrum of solvation power as its density is strongly dependent upon temperature and pressure. Temperature changes of tens of degrees or pressure changes by tens of atmospheres can change a compound's solubility in a supercritical fluid by an order of magnitude or more. This feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows a wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

A material at conditions that border its supercritical state will have properties that are similar to those of the substance in the supercritical state. These so-called "near-critical" fluids are also useful for the practice of this invention. For the purposes of this invention, a near-critical fluid is defined as a fluid which is (a) at a temperature between its critical temperature ($T_c$) and 75% of its critical temperature and at a pressure at least 75% of its critical pressure, or (b) at a pressure between its critical pressure ($P_c$) and 75% of its critical pressure and at a temperature at least 75% of its critical temperature. In this definition, pressure and temperature are defined on absolute scales, e.g., Kelvin and psia. Table 1 shows how these requirements relate to some of the fluids relevant to this invention. To simplify the terminology, materials which are utilized under conditions which are supercritical, near-critical, or exactly at their critical point will jointly be referred to as "SCCNC" fluids.

TABLE 1

Physical Properties of Critical Fluid Solvents

| Fluid | Formula | BP (° C.) | $P_{vap}$ (psia @ 25° C.) | $T_c$ (° C.) | $P_c$ (psia) | 0.75 $T_c$ (° C.) | 0.75 $P_c$ (psia) |
|---|---|---|---|---|---|---|---|
| Carbon dioxide | $CO_2$ | −78.5 | 860 | 31.1 | 1070 | −45.0 | 803 |
| Nitrous oxide | $N_2O$ | −88.5 | 700 | 36.5 | 1051 | −41.0 | 788 |
| Propane | $C_3H_8$ | −42.1 | 130 | 96.7 | 616 | 4.2 | 462 |
| Ethane | $C_2H_6$ | −88.7 | 570 | 32.3 | 709 | −44.1 | 531 |
| Ethylene | $C_2H_4$ | −103.8 | NA | 9.3 | 731 | −61.4 | 548 |
| Freon 11 | $CCl_3F$ | 23.8 | 15 | 198.1 | 639 | 80.3 | 480 |
| Freon 21 | $CHCl_2F$ | 8.9 | 24 | 178.5 | 750 | 65.6 | 562 |
| Freon 22 | $CHClF_2$ | −40.8 | 140 | 96.1 | 722 | 3.8 | 541 |
| Freon 23 | $CHF_3$ | −82.2 | 630 | 26.1 | 700 | −48.7 | 525 |

Notes:
BP = Normal boiling point;
$P_{vap}$ = Vapor pressure

A viable method for controlled release involves the use of degradable or erodable polymers. These are typically formulated as microparticles or microspheres with a size ranging from a maximum of 50 μm down to approximately 0.1 μm. Following administration via ingestion or injection, the polymer is slowly eroded by body fluids to yield biocompatible breakdown products. Concurrently, drug is released from the particle by diffusion through the polymer matrix as well as by surface erosion.

A commonly used bioerodable polymer is of the poly (hydroxyacid) type, in particular poly(L-lactic acid), poly (D,L-lactic acid), poly(glycolic acid), and copolymers thereof. A typical copolymer used for microsphere/microparticle formation is poly(lactide-co-glycolide), abbreviated as PLGA. These materials are broken down in the body to the non-toxic products lactic acid and glycolic acid, and have been approved by the Food and Drug Administration for use as resorbable sutures, in bone implants, and as controlled release microspheres. Other polymers being utilized include poly(fumaric anhydride) and poly(sebacic anhydride). Mathiowitz, E., Jacob, J. S., Jong, Y. S., Carino, G. P., Chickering, D. E., Chaturvedi, P., Santos, C. A., Vijayaraghavan, K., Montgomery, S., Bassett, M. and Morrell, C., Biologically Erodable Microspheres as Potential Oral Drug Delivery Systems, *Nature*, 386:410–414, 1997.

The use of polymeric microspheres for controlled drug delivery has been the subject of a number of reviews. Langer, R., Cima, L. G., Tamada, J. A. and Wintermantel, E.: "Future Directions in Biomaterials," *Biomaterials*, 11:738–745, 1990, the entire teachings of which are incorporated herein by reference.

A typical copolymer used for microsphere/microparticle formation is poly(lactide-co-glycolide), abbreviated as PLGA. Conventional drug-containing PLGA microspheres are prepared by a solvent evaporation method using a double emulsion technique which involves four major sequential steps: (1) mixing of PLGA (in methylene chloride) with drug (in water) followed by sonication to obtain a water-in-oil (W/O) emulsion; (2) mixing of W/O with a second aqueous PVA solution followed by sonication to obtain (water-in-oil)-in-water emulsion; (3) solvent evaporation causing microspheres to harden; and (4) collection of microspheres by centrifugation followed by three washing steps.

In an alternative process, a five step process is employed: (1) protein particles are first milled into a fine powder in the 1 μm to 10 μm range; (2) a suspension of the protein particles is made in a solution of PLGA in methylene chloride, ethyl acetate or DMSO; (3) the organic solvent/PLGA/protein mixture is injected into liquid nitrogen to form frozen microspheres; (4) the frozen microspheres are transferred into ethanol at −100° C. to back-extract the organic solvent three times; and (5) the microspheres are filtered, lyophilized and packaged.

In one embodiment of the present invention, a method of making polymeric spheres comprising the steps of providing a polymer solution of a polymeric material dissolved in a first fluid is disclosed. The apparatus used is similar to that depicted in FIG. 1. In one aspect, the first fluid comprises a supercritical, critical or near-critical fluid. Next, the polymer solution is depressurized as the polymer solution exits one or more orifices of the apparatus in the presence of a low solubility fluid. The low solubility fluid has low volatility and the polymeric material is in a concentration which exceeds the solubility of the polymeric material in the low solubility fluid. The polymeric material forms spheres and the first fluid is removed during depressurization.

The polymeric spheres of the present invention have an average diameter of between 0.01 and 10.0 microns and, in one aspect, between 0.1 and 1.0 microns. The narrow range of diameter of the microspheres and nanospheres that can be attained with the present method is unusual and surprising.

In one aspect, the polymeric material is selected from one or more of the group of polymers consisting of poly(L-lactic acid), poly(D, L-lactic acid), poly(glycolic acid) and carboxylic acid and ester derivatives thereof, poly(fumaric anhydride) and poly(sebacic anhydride).

In one aspect, the first fluid can comprise carbon dioxide, nitrous oxide, ethylene, ethane, propane and fluorohydrocarbons. The first fluid can also contain modifiers. Examples of such modifiers include, but are not limited to, methanol, ethanol, propanol, butanol, methylene chloride, ethyl acetate and acetone.

In one aspect, the temperature and pressure for a SCCNC comprising carbon dioxide are a temperature in the range of about 10 to about 60° C. and a pressure in the range of about 1,000 to about 5,000 psig.

The present invention also relates to methods used to incorporate bioactive materials in polymeric spheres.

In one embodiment, a polymeric material is contacted with a first fluid. This first fluid comprises a critical, supercritical, or near critical fluid with or without one or more cosolvents. This first admixture of polymeric material and first fluid are admixed with a second fluid forming a second admixture, wherein the second fluid comprises a bioactive or therapeutic agent (such as a pharmaceutical, peptide, protein, nucleic acid, and other biological molecules well known to those skilled in the art). (As used herein, the term "bioactive" refers to compositions which cause a change or modification of a living organism in the nature of pharmaceuticals, drugs, toxins, biocides and the like.) This second fluid can comprise a critical, supercritical, or near critical fluid together with a cosolvent such as an alcohol, an aqueous solvent such as distilled water or mixtures thereof. The second admixture is subjected to depressurization. This depressurization can be accomplished by releasing the second admixture through an orifice of the apparatus into a medium at or near, for example, atmospheric pressure. In one aspect, the medium into which the second admixture is released is a third fluid. This third fluid is a low solubility solvent. During depressurization, high volatility solvents such as a critical, supercritical, or near critical fluid are removed from low volatility solvents such as water containing polymeric spheres. Sterile filtration and solvent evaporation can then be used to harvest the polymeric spheres.

In one aspect, the bioactive agent is dissolved in the first fluid or dissolved in, or is held as a suspension or as an emulsion in the second fluid which is combined with the first fluid and polymeric material. In a particular aspect, the fluid used to dissolve or hold the bioactive material is a supercritical, critical or near-critical fluid.

In one aspect, the third fluid (or low solubility fluid) is selected from the group of solvents consisting of water, PVA, PBS, and liquid nitrogen, with or without a cosolvent, such as an alcohol, an aqueous solvent such as distilled water or mixtures of the aforementioned. The third fluid can also contain a chemical agent for stabilizing the polymeric spheres by cross-linkage or other means well known to those skilled in the art. The low solubility fluid can also be comprised of a critical, supercritical or near-critical fluid or mixtures of the aforementioned.

One method of the present invention for making polymeric spheres having an average diameter of between about 0.01 to about 10 microns and a bioactive material comprises the steps of providing a polymer solution of a polymeric material in a first fluid, the first fluid consisting of a supercritical, critical or near-critical fluid. Next, the method comprises the step of providing a bioactive fluid having bioactive material. Next, an admixture of the first solution and the bioactive fluid is formed, to form an admixture solution, the admixture solution comprising a supercritical, critical or near-critical fluid. The admixture solution is depressurized as the admixture solution exits one or more orifices in the presence of a low solubility fluid. The low solubility fluid has low volatility and the polymeric material is in a concentration which exceeds its solubility in this fluid. The polymeric material forms spheres having an average diameter of 0.1 to 1.0 microns which spheres contain the bioactive material as the first fluid is removed during depressurization.

A further embodiment of the present invention features an apparatus for forming one or more polymeric spheres. The apparatus comprises an admixture vessel, a depressurization chamber and an orifice. The admixture vessel is for receiving and containing a polymer solution of a polymeric material in a first fluid, the first fluid consisting of a supercritical, critical or near-critical fluid. The depressurization chamber contains a low solubility fluid and is in fluid communication with the admixture vessel by the orifice. The depressurization chamber receives the polymer solution as said polymer solution exits the orifices in the presence of a low solubility fluid. The low solubility fluid has low volatility and the polymeric material is in a concentration which exceeds its solubility in such fluid. The polymeric material forms spheres and the first fluid is removed during depressurization.

The apparatus is used to make spheres having an average diameter of 0.01 to 10.0 microns.

In one aspect, the admixture vessel receives a bioactive material. The bioactive material is dissolved in a solvent or held as a suspension in a fluid or held in an emulsion. Such bioactive material is incorporated into the spheres during depressurization.

In one aspect, the apparatus further comprises a polymer vessel for forming a solution of a polymer in a supercritical, critical or near-critical fluid. The polymer vessel is in fluid communication with the admixture vessel.

In one aspect, the apparatus further comprises a bioactive material vessel for forming a suspension, solution or emulsion of said bioactive material in a fluid. The bioactive vessel is in communication with the admixture vessel.

Sterile filtration and solvent evaporation can then be used to harvest the polymeric spheres. SCCNC fluids also sterilize the materials in which such fluids are incorporated upon rapid depressurization, such as depressurization through an orifice.

The use of SCCNC fluids allows for easy removal of much of the solvent by mere depressurization. Use of a single apparatus to perform polymer sphere formation and encapsulate therapeutic agents minimizes labor and increases efficiency. Indeed, the entire process can be readily automated. The use of SCCNC fluids allows process conditions to be readily varied by temperature, pressure, or modifier solvents, minimizing equipment needs, processing time, potential for contamination, and loss of yield. The use of SCCNC fluids eliminates the need for toxic organic solvents such as in methylene chloride, ethyl acetate or DMSO and eliminates the presence of these toxic organic solvents in the final product.

The present method an apparatus will be described with respect to FIG. 1 which depicts in schematic form a polymer sphere apparatus, generally designated by the numeral 11. The polymer sphere apparatus is comprised of the following major elements: a polymer vessel 13, a bioactive injection assembly 15, an admixture chamber 17, a depressurization vessel 19, and an orifice nozzle 21.

Polymer vessel 13 is in fluid communication with a SCCNC syringe pump 25 via conduits 27*a* and 27*b*. SCNCC pump 25 is in fluid communication with a source of SCCNC fluid (not shown).

Polymer vessel 13 is also in fluid communication with a modifier syringe pump 31 via conduit 33 which intersects with conduit 27*a* and 27*b* at junction 35. Modifier syringe pump 31 is in communication with a source of modifiers and/or entrainers (not shown).

Polymer vessel 13 is loaded with polymer. And, polymer vessel receives SCNCC fluid from SCNCC pump 25 via conduits 27*a* and 27*b*. Polymer vessel 13 receives modifiers and/or entrainers from Modifier pump 31 via conduit 33. Polymer is dissolved in the SCNCC fluid and modifier to form a polymer solution.

Polymer vessel 13 is in fluid communication with admixture chamber 17 via conduits 37 and 39. Admixture chamber 17 is also in fluid communication with bioactive injection assembly 15. Bioactive injection assembly 15 comprises bioactive syringe pump 43, a source of bioactive material (not shown) and conduit 45. Bioactive syringe pump 43 is in communication with a source of bioactive material and pressurizes and compels such material through conduit 45. Conduit 45 is in communication with admixture chamber via conduits 39 which intersects conduit 45 at junction 47. Preferably junction 47 is a mixing "T".

Admixture vessel 17 is in the nature of an inline mixer and thoroughly mixes incoming streams from the polymer vessel 13 and bioactive injection assembly 15. Admixture vessel 17 is in communication with orifice nozzle 21 via conduit 49. Orifice nozzle 21 is in the nature of a back pressure regulator and has a nozzle defining one or more orifices which discharge into depressurization vessel 19 via conduit 51. Preferably orifice nozzle 21 controls pressure and decompression rates.

The operating pressure of the system can be preset at a precise level via a computerized controller (not shown) that is part of the syringe pumps. Temperature control in the system is achieved by enclosing the apparatus 11 in ¼" Lexan sheet while utilizing a Neslab heating/cooling system coupled with a heat exchanger (not shown) to maintain uniform temperature throughout the system.

In a typical experimental run, polymeric materials were first packed into the polymer vessel 13. SCCNC and an ethanolic solution of insulin were charged into the SCNCC syringe pumps 25 and 31, respectively, and brought to the desired operating pressure. In the alternative, a ethanol solution of insulin is charged into bioactive syringe pump 43.

The system was then pressurized with the SCCNC (supercritical fluid (SCF) and cosolvent) via SCNCC syringe pump 25 to the pressure level equal to that set in modifier syringe pump 31 and bioactive syringe pump 43, and maintained at this level with the nozzle orifice 21. The dynamic operating mode for all pumps were set so that each pump can be operated at its own desired flow rate. The SCCNC stream flowed through the polymer vessel 13, dissolved polymer and contacted the insulin stream at junction 47. The mixture of SCCNC, insulin and polymeric materials was then passed through admixture chamber 17 for further mixing. Finally, the mixed solution entered orifice nozzle 21 and was injected into a 0.1% PVA aqueous solution in the depressurization vessel 19. As a result of supercritical fluid decompression, polymeric spheres containing insulin are formed in the PVA aqueous solution and the expanded supercritical fluid exited the system via a vent line on the depressurization vessel 19.

EXAMPLES

For preliminary experiments, 50:50 mixtures of poly(D, L-lactic glycolic acid) with molecular weights of 3,000, 50,000 and 100,000 (Sigma Chemicals, St. Louis, Mo.) were utilized. For most microsphere and some solubility experiments, Medisorb® biodegradable polymers (Alkermes, Inc., Cincinnati, Ohio) were utilized. The specifications on the Medisorb polymers are listed in Table 2. "A" indicates that the polymers contain a free carboxylic acid group on the carboxyl end of the polymer chain; "M" indicates an ester end group.

TABLE 2

Specifications of Medisorb ® Biodegradable Polymers

| Medisorb Polymer | Inherent Viscosity (dL/g) | Approx. MW (Kd) | DL-lactide/glycolide mole ratio |
|---|---|---|---|
| 5050DL2A | 0.15 | 12.3 | 53/47 |
| 5050DL2M | 0.18 | 17.3 | 54/46 |
| 5050DL3A | 0.25–0.33 | 20–28 | 54/46 |

Other materials utilized include insulin, cytochrome-C, tetanus and diphtheria toxoids, ethyl alcohol (USP grade), distilled water, and polyvinyl alcohol (PVA).

Example 1

SCCNC Polymer Microspheres/Nanospheres Formed with Near-Critical Propane

Polymer microspheres/nanospheres were formed with 50:50 PLGA obtained from Sigma Chemicals (St. Louis, Mo.) in the SCCNC polymer sphere apparatus running in the continuous mode. The polymer microspheres/nanospheres were formed by injecting the SCCNC polymer solution into distilled water. The resulting product was observed under a light microscope, and the particle sizes were measured in a Coulter 4MD sub-micron particle size analyzer. The volume of distilled water used in PMF-03a was about half of that used in PMF-01 resulting in a more concentrated microsphere solution and a different particle size distribution. Some of these results are presented in Table 3.

TABLE 3

SCCNC Polymer Microspheres/Nanospheres Formed with 50:50 PLGA at 40° C.

| Run No. | SCCNC | Pressure (psig) | Flow Rate (mL/min) | Small Size (nm)/% | Medium Size (nm)/% | Large Size (nm)/% |
|---|---|---|---|---|---|---|
| PMF-01 | $C_3H_8$ | 2,000 | 1.0 | 99 (26%) | 336 (74%) | |
| PMF-02a | $C_3H_8$ | 4,000 | 1.0 | | 120 (34%) | 2,120 (66%) |
| PMF-02b | $C_3H_8$ | 5,000 | 3.0 | 33 (57%) | 282 (15%) | 10,000 (29%) |
| PMF-03a | $C_3H_8$ | 2,000 | 1.0 | | 291 (76%) | 1,770 (24%) |
| PMF-03b | $C_3H_8$ | 2,000 | 4.0 | | 169 (33%) | 852 (67%) |

Example 2

Protein Antigencity in Polymer Microspheres Formed by Different SCCNC

Experiments were performed to encapsulate tetanus toxoid (TT) and diphtheria toxoid (DT) vaccine antigens in 50:50 PLGA polymer microspheres formed by SCCNC carbon dioxide and propane. In these tests, DT and TT were each separately treated with supercritical carbon dioxide with 10% (v/v) cosolvent ethanol, and near-critical propane in the presence of PLGA. The pressure and temperature were around 3,000 psig and 30–35° C. respectively. The protein and antigenicity activities were performed by micro BCA assay and a sandwich-type capture ELISA [Gupta, R. K., Siber, G. R., Alonso, M. J. and Langer, R., in *Modern Approaches To New Vaccines Including Prevention of AIDS*. Ed. by Ginsberg, H. S., Brown, F., Chanock, R. M. and Lerner, R. A. Cold Spring Harbor Laboratory, Press, 1993] assay. The results of this study are summarized in Table 4.

TABLE 4

Protein Content and Antigencity of Tetanus Toxoid and Diphtheria Toxoid in PLGA Polymer Microspheres formed by Different SCCNC

| Sample No. | Toxoid | SCCNC | Protein (mg/mL) | ELISA (Lf/mL) |
|---|---|---|---|---|
| 1 | Diphtheria | Control | 21.07 | 7.35 |
| 2 | Diphtheria | $CO_2$/ethanol | 1.49 | 0.13 |
| 3 | Diphtheria | $C_3H_8$ | 18.63 | 6.55 |
| 4 | Tetanus | Control | 30.44 | 9.0 |
| 5 | Tetanus | $CO_2$/ethanol | 9.81 | 0.44 |

Both diphtheria and tetanus toxoids lost most of their antigenicity after being treated with SCCNC carbon dioxide/ethanol mixtures. These losses are probably due to the fact that the acid/base equilibrium shifted due to the formation of carbonic acid when the aqueous protein is exposed to carbon dioxide. This shift can drastically reduce pH if the solution is insufficiently buffered. Both diphtheria and tetanus toxoids will denature at pH levels below 5.0. Thus, carbon dioxide may not be the best candidate for a SCCNC solvent for acid pH sensitive proteins. Propane, on the other hand, did little damage to the diphtheria toxoid because it has negligible impact on the acid/base equilibrium of the aqueous protein.

Example 3

Protein (Insulin) Encapsulation by SCCNC Polymer Microspheres/Nanospheres

Experiments were conducted to encapsulate insulin in polymer microspheres/nanospheres utilizing supercritical carbon dioxide. Insulin, which has an isoelectric point of 3.65, is stable at acid pHs. In these experiments, a feed solution of 0.1 mg/mL insulin in 90% ethanol: 10% water was utilized. The supercritical carbon dioxide was pumped at a rate of 1 mL/min, the cosolvent pump at 0.1 mL/min, and the insulin solution at 0.5 mL/min. The resultant mixture was injected into 8 mL of 1% PVA solution for 30 minutes. The results of these experiments are summarized in Table 5.

TABLE 5

Polymer Microspheres/Nanospheres Formed with Medisorb Polymers and Insulin in SCCNC Carbon Dioxide/Cosolvent at 3,000 psig and 50° C.

| Run No. | Polymer | SCCNC | Small Size (nm) | Medium Size (nm) | Large Size (nm)/% |
|---|---|---|---|---|---|
| MS-09 | DL2A | $CO_2$/ethanol | | 750 (22%) | 5,250 (77%) |
| MS-10 | DL2M | $CO_2$/ethanol | | 634 (100%) | |
| MS-11 | DL3A | $CO_2$/ethanol | | 300 (49%) | 10,000 (51%) |
| MS-12 | DL2A | $CO_2$/acetone | | 326 (100%) | |

The data in Table 5 indicates that the Medisorb DL2M and DL2A bioadhesive polymers formed relatively uniform particle size distributions in the SCCNC $CO_2$/ethanol and SCCNC $CO_2$/acetone systems, respectively, at 3,000 psig and 50° C.

Example 4

Release of Cytochrome-C from SCCNC Polymer Microspheres/Nanospheres

In order to establish conditions for the encapsulation of proteins in uniform microspheres and their release characteristics, several experiments were conducted to encapsulate cytochrome-C in polymer microspheres/nanospheres utilizing supercritical carbon dioxide. In these experiments, a feed solution of 0.1 mg/mL cytochrome-C in 99% ethanol: 1% water was utilized. The supercritical carbon dioxide was pumped at a rate of 1.0 mL/min, the cosolvent pump at 0.1 mL/min, and the cytochrome-C solution at 0.5 mL/min. The resultant mixture was injected into 8 mL of 1% PVA solution for 30 minutes. The results of some of these experiments are summarized in Table 6.

TABLE 6

Polymer Microspheres/Nanospheres Formed with Medisorb Polymers and Cytochrome-C in SCCNC Carbon Dioxide and Propane at 3,000 psig

| Run No. | Polymer | SCCNC | Temp. (°C.) | Small Size (nm) | Medium Size (nm) | Large Size (nm) |
|---|---|---|---|---|---|---|
| MS-19 | DL3A | $CO_2$/10% ethanol | 45 | | 318 (100%) | |
| MS-21 | DL2A | $CO_2$/10% ethanol | 45 | | 292 (100%) | |
| MS-22 | DL2A | $CO_2$/10% acetone | 45 | | 267 (100%) | |
| MS-23 | DL2M | $CO_2$/10% ethanol | 45 | | 239 (100%) | |
| MS-24 | DL2A | $C_3H_8$/10% acetone | 30 | | 187 (100%) | |
| MS-25 | DL2A | $C_3H_8$/3% acetone | 40 | | 418 (100%) | |

Some of the size distributions were quite narrow while others were broad. Some of the charts indicate the presence of "dust" which are particles that are larger than 10 micron in size. Most of these particles, from microscopic observations, appear to be excess polymer. These large polymer particles were removed by vacuum filtration prior to solvent evaporation and drying to harden the polymer microspheres/nanospheres. In experiments MS-24 and MS-25, the supercritical fluid and cosolvent pumps were kept in operation for 180 minutes after the feed pump was turned off to ensure that all the protein had been displaced from the high pressure circulation loop.

Figure 2:
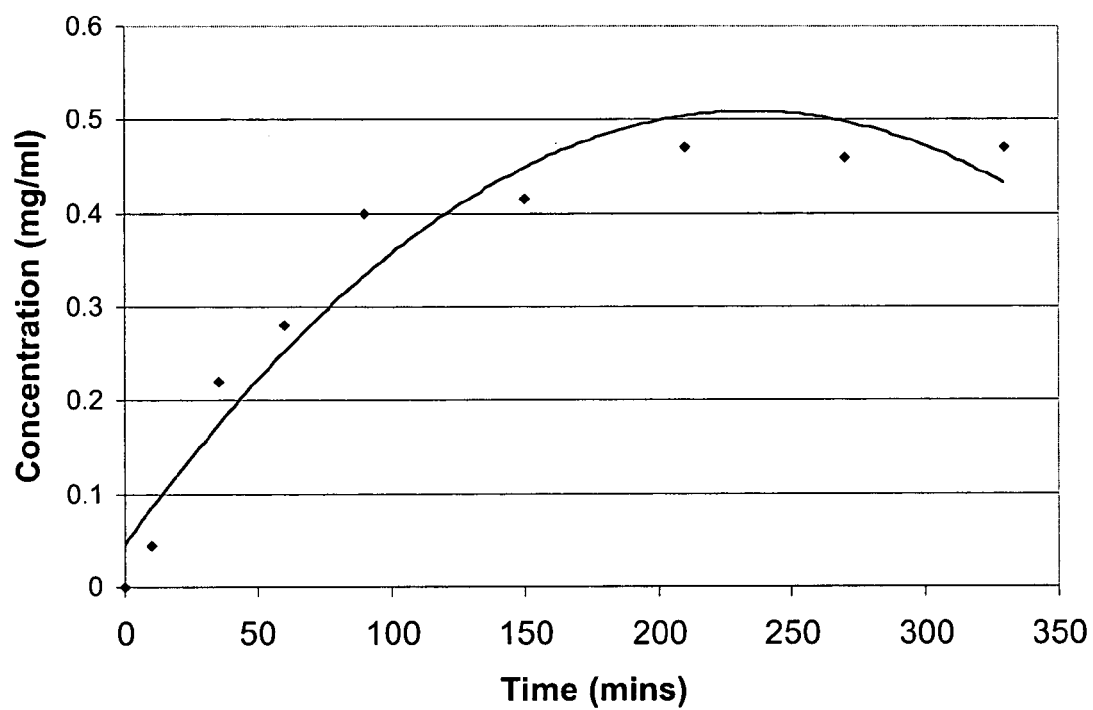
FIG. 2 shows the in vitro time release characteristics of cytochrome-C from SCCNC polymer spheres; and,
FIG. 3 shows the in vitro time release characteristics of insulin from SCCNC polymer nanospheres.

The release characteristics of MS-25 were evaluated by suspending the dried microspheres in 4 mL of PBS at a pH of 7.4. Absorption of the solution was then measured at 408 nm and over the 350 to 450 nm range at different time intervals. Concentration was determined from a standard curve. The release characteristics of MS-25 over a 5 hour period is shown in FIG. 2.

Example 5

In Vitro Release of Insulin from SCCNC Polymer Microspheres/Nanospheres

Figure 3:
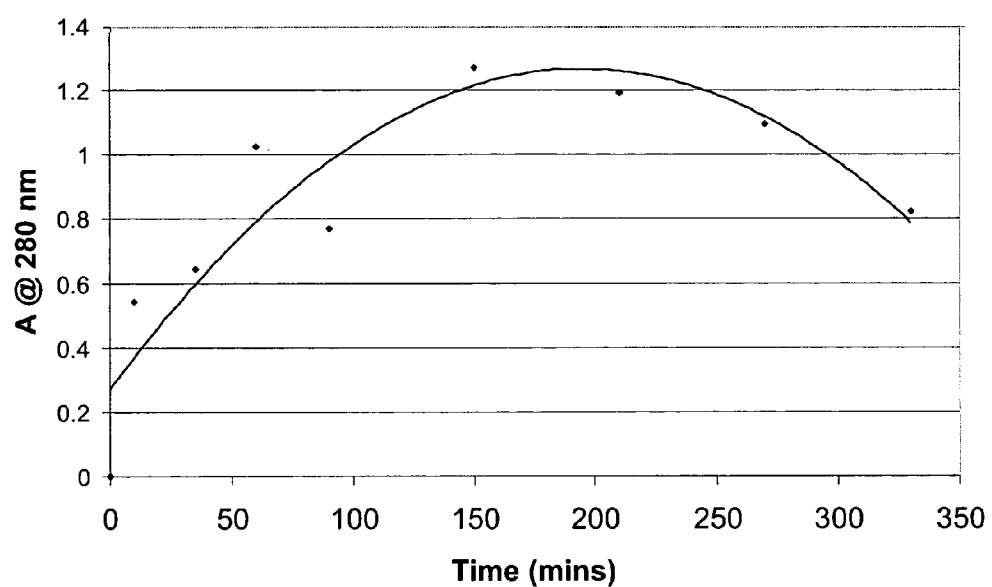

In this example, a feed solution of 0.1 mg/mL insulin in 90% ethanol: 10% water was utilized. Supercritical carbon dioxide was pumped at a rate of 1.0 mL/min, the cosolvent pump at 0.1 mL/min, and the insulin solution at 0.5 mL/min. The resultant mixture was injected into 8 mL of 1% PVA solution for 30 minutes. The supercritical fluid and cosolvent pumps were kept in operation for 180 minutes after the feed pump was turned off to ensure that all the protein had been displaced from the high pressure circulation loop. The release characteristics of insulin in this experiment MS-27 was evaluated by suspending the dried microspheres in 4 mL of PBS at a pH of 7.4. Absorption of the solution was then measured at 280 nm and over the 250 to 350 nm range at different time intervals. The release characteristics of MS-27 over a 5-hour period are shown in FIG. 3.

Example 6

In Vivo Release of Insulin from SCCNC Polymer Microspheres/Nanospheres

A preliminary study with SCCNC polymer nanoencapsulated insulin was conducted in diabetic rats. Three groups of four chronic diabetic BB/Wor male rats were used to evaluate efficacy on nanoencapsulated insulin (MS-29). One group [A] was given 2 ml of the test formulation (MS-29) using the standard gavage method. The second group [B] received oral non-encapsulated insulin, administered by gavage at the concentration based on the animals' day of diabetes onset. A third group [C] received injected insulin (PZI, Eli Lilly) therapy at the dose consistent with their day of onset of diabetes. The animals were bled prior to treatment and at 0.5, 1, 2, 4, 8, and 16 hrs after treatment. The results are summarized in Table 7.

TABLE 7

Percent Change in Glucose Concentration in Diabetic Rats (mg/dL)

| Post-Treatment Time | A Test Article (MS-29) | B Oral Insulin | C Injected Insulin |
|---|---|---|---|
| 0.5 hr | −22.1% | +2.9% | −47.4% |
| 1 hr | −22.8% | −4.6% | −62.7% |
| 2 hr | −22.1% | −24.4% | −71.8% |
| 4 hr | +17.6% | +2.8% | −37.9% |
| 8 hr | +13.5% | +7.5% | −48.5% |
| 16 hr | +35.4% | +47.3% | −37.6% |

The results of this in vivo study [Column A] showed a significant decrease in glucose levels at 0.5, 1 and 2 hours after the oral administration of SCCNC polymer nanoencapsulated insulin. While the duration was only for 2 hours, it was immediate and consistent. The duration can be improved by increasing dosage levels and/or polymer molecular weight/type that will determine the integrity of the SCCNC polymer nanospheres.

Non-encapsulated insulin given orally by gavage only showed a statistical decrease in the level of glucose at one time point, 2 hours [Column B]. At all other times, oral insulin did not statistically decrease the levels of glucose in diabetic rats.

The positive control, injected insulin in Column C, caused a statistical decrease in glucose levels at all times measured post treatment.

It is intended that the matter contained in the preceding description be interpreted in an illustrative rather than a limiting sense.

What is claimed is:

1. A method of making polymeric spheres having an average diameter of between 0.01 and 10.0 microns, comprising the steps of:

a) providing a polymer solution of a polymeric material dissolved in a first fluid, said first fluid consisting of a supercritical, critical or near-critical fluid; and, b) depressurizing said polymer solution as said polymer solution exits one or more orifices in the presence of a low solubility fluid, said low solubility fluid having low volatility and said polymeric material in a concentration which exceeds said solubility of said polymeric material in said low solubility fluid, said polymeric material forming spheres having an average diameter between 0.01 and 10.0 microns and said first fluid removed during depressurization wherein said low solubility fluid is selected from the group of solvents consisting of PVA, PBS, liquid nitrogen, distilled water and an alcohol.

2. The method of claim 1 wherein said spheres have an average diameter of between 0.1 to 1.0 microns.

3. The method of claim 1 wherein said polymer solution has a bioactive material, said bioactive material dissolved in said polymer solution or held in said polymer solution as a suspension or emulsion.

4. The method of claim 3 wherein said bioactive material is dissolved in said first fluid.

5. The method of claim 3 wherein said bioactive material is held as a suspension in said polymer solution.

6. The method of claim 3 wherein said bioactive material is held as an emulsion in said polymeric solution.

7. The method of claim 3 wherein said bioactive material is dissolved in a second fluid and said second is combined with said first fluid and polymeric material.

8. The method of claim 7 wherein said second fluid is a supercritical, critical or near-critical fluid.

9. The method of claim 7 wherein said bioactive material is held as a suspension in said second fluid.

10. The method of claim 3 wherein said bioactive material is held as an emulsion in said second fluid.

11. The method of claim 1 wherein said polymer solution is depressurized to ambient pressure.

12. The method of claim 1 wherein said polymer is selected from one or more of the group of polymers consisting of poly(L-lactic acid), poly(D, L-lactic acid), poly(glycolic acid) and carboxylic acid and ester derivatives thereof, poly(fumaric anhydride) and poly(sebacic anhydride) and derivatives thereof.

13. A method of making polymeric spheres having an average diameter of between 0.01 and 10.0 microns, comprising the steps of:

a) providing a polymer solution of a polymeric material in a first fluid, said first fluid consisting of a supercritical, critical or near-critical fluid;

b) providing a second solution of a bioactive material in a second fluid;

c) forming an admixture of said first solution and said second solution to form a third solution, said third solution comprising a supercritical, critical or near-critical fluid;

d) depressurizing said third solution as said third solution exits one or more orifices in the presence of a low solubility fluid, said low solubility fluid having low volatility and said polymeric material in a concentration which exceeds said solubility of said polymeric material in said low solubility fluid, said polymeric material forming spheres having an average diameter of 0.01 to 10.0 microns, said spheres containing said bioactive material and said first fluid removed during depressurization wherein said low solubility fluid is selected from the group of solvents consisting of PVA, PBS, liquid nitrogen, distilled water and an alcohol.

14. The method of claim 13 wherein said spheres have an average diameter of between 0.1 to 1.0 microns.

15. An apparatus for forming one or more polymeric spheres having an average diameter of between 0.01 and 10.0 microns, comprising:

a) an admixture vessel for receiving a polymer solution which polymer solution is a polymeric material dissolved in a first fluid, said first fluid consisting of a supercritical, critical or near-critical fluid;

b) an orifice nozzle in communication with said admixture vessel for receiving said polymer solution;

c) a depressurization vessel containing a low solubility fluid in communication with said orifice nozzle for receiving a stream of polymer solution as said polymer solution exits one or more orifices in the presence of said low solubility fluid, said low solubility fluid having low volatility and said polymeric material in a concentration which exceeds said solubility of said polymeric material in said low solubility fluid, said polymeric material forming spheres having an average diameter of 0.01 to 10.0 microns and said first fluid removed during depressurization d) a polymer vessel for forming a solution of a polymer in a supercritical, critical or near critical fluid, said polymer vessel in fluid communication with said admixture vessel; and, e) a bioactive material vessel for forming a suspension, solution or emulsion of said bioactive material in said polymer solution, said bioactive vessel in communication with said admixture vessel.

16. The apparatus of claim 15 wherein said spheres have an average diameter of between 0.1 to 1.0 microns.

17. The apparatus of claim 15 wherein said admixture vessel receives a bioactive material, said bioactive material dissolved in a solvent or held as a suspension in a fluid or held in an emulsion, and said bioactive material incorporated into said spheres during depressurization.

* * * * *